(12) United States Patent
Loscutova et al.

(10) Patent No.: US 10,011,705 B2
(45) Date of Patent: Jul. 3, 2018

(54) ALUMINA COMPOSITIONS AND METHODS FOR PRODUCING SAME

(71) Applicant: Sasol Performance Chemicals GmbH, Hamburg (DE)

(72) Inventors: Ryan Loscutova, Houston, TX (US); Maria Roberta Rabaioli, Westlake, LA (US)

(73) Assignee: Sasol Performance Chemicals GmbH, Hamburg (DE)

( * ) Notice: Subject to any disclaimer, the term of this patent is extended or adjusted under 35 U.S.C. 154(b) by 11 days.

(21) Appl. No.: 15/110,652

(22) PCT Filed: Jan. 21, 2015

(86) PCT No.: PCT/IB2015/000272
§ 371 (c)(1),
(2) Date: Jul. 8, 2016

(87) PCT Pub. No.: WO2015/110913
PCT Pub. Date: Jul. 30, 2015

(65) Prior Publication Data
US 2016/0340496 A1 Nov. 24, 2016

Related U.S. Application Data

(60) Provisional application No. 61/929,782, filed on Jan. 21, 2014.

(51) Int. Cl.
| | | |
|---|---|---|
| C09C 1/40 | (2006.01) | |
| C08K 9/04 | (2006.01) | |
| C08K 9/08 | (2006.01) | |
| C07F 5/06 | (2006.01) | |

(52) U.S. Cl.
CPC ............ *C08K 9/04* (2013.01); *C07F 5/069* (2013.01); *C08K 9/08* (2013.01); *C09C 1/407* (2013.01); *C01P 2002/60* (2013.01); *C01P 2002/76* (2013.01); *C01P 2002/82* (2013.01); *C01P 2002/88* (2013.01); *C01P 2004/03* (2013.01); *C01P 2004/64* (2013.01); *C01P 2006/12* (2013.01); *C08K 2201/011* (2013.01)

(58) Field of Classification Search
USPC .......................................... 523/202; 524/437
See application file for complete search history.

(56) References Cited

U.S. PATENT DOCUMENTS

| | | | | |
|---|---|---|---|---|
| 4,420,341 A | * | 12/1983 | Ferrigno | ............... C08K 9/04 106/457 |
| 6,986,943 B1 | * | 1/2006 | Cook | ..................... B01J 2/30 427/214 |
| 2005/0239945 A1 | | 10/2005 | Martin et al. | |
| 2007/0098990 A1 | | 5/2007 | Cook et al. | |
| 2007/0167562 A1 | | 7/2007 | Zhou et al. | |
| 2015/0079450 A1 | * | 3/2015 | Wensley | ............ H01M 2/166 429/144 |

FOREIGN PATENT DOCUMENTS

| | | |
|---|---|---|
| CN | 102115619 | 7/2011 |
| CN | 102352137 | 2/2012 |

* cited by examiner

*Primary Examiner* — Tae H Yoon
(74) *Attorney, Agent, or Firm* — Bushman Werner, P.C.

(57) ABSTRACT

A method of producing functionalized surface-modified alumina by adding an organic modifier comprising acrylic acid to alumina and drying the alumina to covalently bond the organic modifier to the surface of the alumina. The functionalized surface-modified alumina being uniformly dispersible in organic polymer to form single crystallites of functionalized surface-modified alumina in the polymer.

16 Claims, 6 Drawing Sheets

ALUMINA COMPOSITIONS AND METHODS FOR PRODUCING SAME

CROSS REFERENCE TO RELATED APPLICATION

This application is a national phase of PCT/IB2015/000272 filed Jan. 21, 2015, which claims priority to U.S. Application No. 61/929,782 filed on Jan. 21, 2014, the disclosures of which are incorporated herein by reference for all purposes.

FIELD OF THE INVENTION

The present invention relates to a method(s) for producing a functionalized, surface-modified alumina composition. In particular, the present invention relates to a method of producing functionalized, surface-modified alumina which is dispersible into nano-sized particles in an organic polymer.

BACKGROUND OF THE INVENTION

The use of inorganic particles in polymeric materials to improve various properties is well known in the art. The method of dispersing inorganics throughout the polymeric materials is generally accomplished by extrusion and other mechanical high shear processes. When dispersing inorganics in polymers, the goal is to achieve a homogeneous dispersion of extremely small sized particles. In this regard, it has proven difficult to achieve a homogeneous dispersion of inorganic particles when the particles have a particle size of less than 100 nm. When the size of the particles are reduced to the nanometer size range, the surface area of the inorganic particles in the polymer increases by an order of magnitude, thus increasing the interactions between the inorganic particles and the polymer by an order of magnitude. This increased interaction in turn significantly increases viscosity of the polymer making it more difficult to homogeneously disperse the inorganic particles.

Boehmite aluminas, particularly those derived from alkoxide precursors, can be produced in high purity via effective control of crystallite size and provide a source of thermally stable nano-particles of high surface area and controlled porosity. According to U.S. Publication 2005/0239945, incorporated herein by reference for all purposes, alkoxide derived boehmites which have been surface-modified with certain sulfonic acid modifiers produce nano-sized particles dispersible in a media. Published accounts also demonstrate that boehmite alumina can be surface-modified with organic saturated and unsaturated carboxylic acids to produce crystallites having an average size of 200-300 nm.

Acrylic acid has also been used to modify inorganics, particularly to couple calcium carbonate with polypropylene. However, acrylic acid was not effective at dispersing the calcium carbonate in a nano-sized dimension.

It is known in the art that alumina dispersions can be obtained by electric charge through the addition of mineral and organic acids. These types of alumina dispersions can be easily dispersed in aqueous systems and form stable sols due to electrostatic stabilization. This electrostatic stabilization is due to an electric charge on the alumina surface caused by the adsorption of protons which are produced from an acidic dissociation mechanism.

It is also known in the art that alumina can form dispersions in organic systems including organic acids and their salts due to a mechanism of electro-steric stabilization. For example alumina dispersions can be obtained by the addition of organic carboxylic acids and the ensuing deprotonation of the organic acid and adsorption of the carboxylate anion (COO—) through an electrostatic retention mechanism. Electro-steric mechanisms can improve the wetting of the alumina particles and their incorporation into a polymer, but loosely bound adsorbed species can also revert or desorb from the surface, and compete with traces of residual water adsorbed on the surface of alumina. Because of the hydrophilic nature of the alumina surface these effects will reduce the solubility of the alumina particles in polymeric media and thus reduce the ability to disperse the alumina particles. Thus, rather than containing fully dispersed alumina, the polymer will contain subdivided alumina particles in the form of larger agglomerates comprising several alumina crystals, thus reducing the number of interfaces and the performance of the polymer.

It is further known that products different from alumina, for example alumoxane, can be prepared by digestion, i.e., decomposition to small fragments, of pseudoboehmite with a very large excess of a carboxylic acids of small molecular weight, e.g. hexanoic acid (see A. R. Barron, *J. Mater. Chem.* 5(2) (1995) 331-341). The preparation of such alumoxanes is carried out in organic solvents as they require a total absence of water. Additional process steps are thus required such as an extended filtration process to wash out the excess organic solvent and distillation under vacuum to remove unreacted volatile species.

An object of the present invention is to overcome the drawbacks of the methods indicated above. Another object of the present invention is to provide a process for preparing functionalized surface-modified alumina compositions, which include an aqueous phase. Another object is to obtain a functionalized surface-modified alumina composition that is able to dissolve in organic polymer forming nano dispersions which are characterized by nano size particles in the form of single alumina crystals (measured by means of electron microscopy).

The disadvantages of the prior art are overcome by the present invention and a new method to modify and functionalize the surface of an alumina composition as well as a new method of producing functionalized, surface-modified alumina which is dispersible into nano-sized particles in an organic polymer are hereinafter disclosed.

SUMMARY OF THE INVENTION

According to one aspect of the invention there is provided a method for producing a functionalized surface-modified alumina including the steps of:
  i) providing an alumina composition;
  ii) adding an organic modifier including an acrylic acid composition to the alumina composition to produce a surface-modified alumina composition; and
  iii) drying the surface-modified alumina composition to produce a functionalized, surface-modified alumina composition wherein the organic modifier is covalently bonded to the surface-modified alumina composition.

According to a further aspect of the invention, there is provided a method for producing a functionalized surface-modified alumina including the steps of:
  i) providing an alumina composition in an aqueous slurry form, the slurry having a pH of from 8 to 10;
  ii) adding an organic modifier including an acrylic acid composition to the slurry to form an acidic slurry having a pH of 2.5 to 4.0;

iii) adding a base additive to the acidic slurry to increase the pH of the acidic slurry to a pH of 4.2 to 5.0 to form a surface-modified alumina composition; and iv) drying the surface-modified alumina composition to produce a functionalized, surface-modified alumina composition wherein the organic modifier is covalently bonded to the surface-modified alumina composition.

According to another aspect of the invention there is provided a method of producing alumina which is dispersible into nanosized, single-particle crystallites in an organic polymer including the steps of:

i) providing the functionalized, surface-modified alumina as prepared according to the process as defined above; and ii) adding the functionalized, surface-modified alumina to a carrier at a temperature of from scientific room temperature to about 300° C.

These and further features and advantages of the present invention will become apparent from the following detailed description, wherein reference is made to the figures in the accompanying drawings.

DETAILED DESCRIPTION OF PREFERRED EMBODIMENTS

Figure 1:
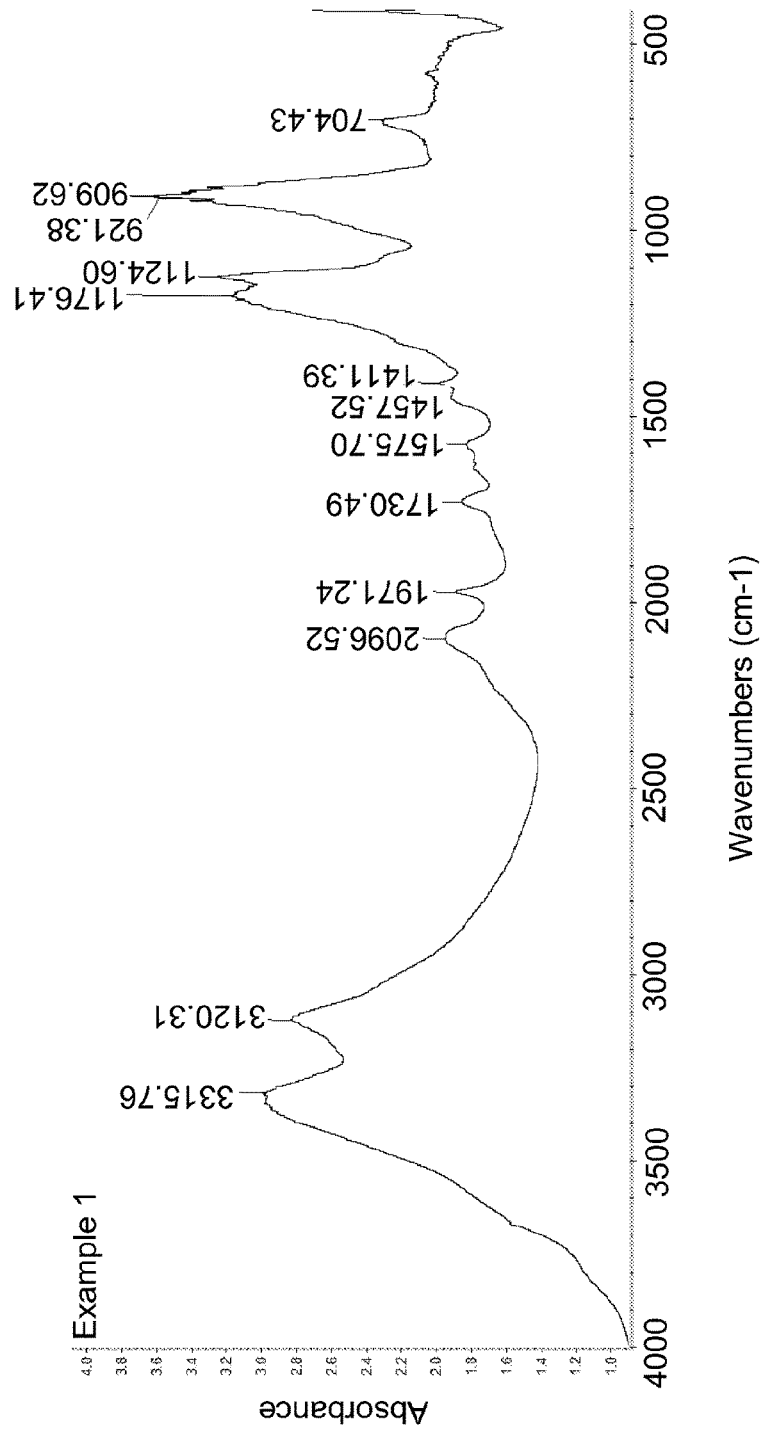
FIG. 1 shows results of a diffuse reflectance infrared fourier transform (DRIFT) spectra analysis based on aluminium-oxygen-carbon stretching band as per Example 1.

As used herein, the term "functionalized surface-modified alumina composition" means that the surface hydroxyl groups of alumina have been transformed into organoaluminum species by the reaction of these hydroxyl groups with the carboxylic groups of the organic modifier through the elimination of water, i.e., drying. The contemplated structure of the organoaluminum species (determined by such methods as infrared spectroscopy) comprises carboxylate-like chemisorbed species with high binding energy. As shown in Formula I below, the high binding energy comes from the two covalent bonds through the two Al atoms which hold the organic modifier to the alumina surface.

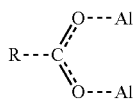

I

These organoaluminum species can be present in combination with acid-base pair sites formed by the interaction between the COOH group of the organic acid and unsaturated Al sites (Lewis centers) which will also be strongly bound and therefore difficult to replace or desorb without specific chemical reactions.

In order to produce the modified alumina of the present invention, a reduction in the loss of the organic modifier during the drying step is essential. As explained below, the organic modifier includes acrylic acid, which due to its light molecular weight and volatility, is more likely to evaporate during the drying step of the invention. As will be shown hereafter, the addition of a base additive to the alumina has been found to be an effective option in the process of the invention to keep the target molecules of the organic modifier on the surface of the alumina composition during the drying. As used herein, the term "target molecules" of the organic modifier constitute the portions of the monomers, dimers, trimers, or oligomers of varying molecular weights that interact with the alumina. In other words, in the case of an oligomer, only a portion of the oligomer may interact with/bond to the alumina. This portion would be the target molecule. It is also possible for the entire molecule to constitute the target molecule, as in the case of monomers and other small molecules which interact entirely with the alumina.

As mentioned briefly above, a base additive can be added to reduce the loss of the organic modifier during drying. While not to be bound by theory, it is believed that in the presence of the ionic strength of the base additive, the polymerizable target molecules of the organic modifier formed new oligomeric groups which then precipitated or attracted efficiently towards the alumina surface. These species were made by reacting the alumina composition under slight acidic conditions with a base additive and removing water to complete the reaction during drying. The intensity of the covalent attachment on the crystallite surface of the alumina was revealed by infrared spectroscopy in the region of the formation of the aluminium-oxygen-carbon chemical bond. The base additive can either be added to the alumina during the preparation process of the surface-modified alumina or it can be provided with the organic modifier solution.

As used herein, the term "scientific room temperature" means a temperature in the region of 20 to 24° C. As used herein, the term "crystallite" means an alumina crystal that is a single crystal (i.e., not twinned, etc.).

The present invention is directed to a method for producing a functionalized, surface-modified alumina composition by modifying a surface of an alumina composition with the addition of an organic modifier such that the organic modifier is covalently bonded to a surface of the surface-modified alumina after a drying step. Optionally, the present invention is directed to a method for producing a functionalized, surface-modified alumina by modifying a surface of an alumina composition in a slurry form with the addition of an organic modifier and a base additive to modify the pH of the slurry and improve the attachment of the organic modifier to the surface of the alumina through covalent bonding after a drying step. The invention is further directed to a method of producing alumina which is dispersible into nano-sized single crystallite particles in an organic polymer by adding the functionalized surface-modified alumina to a carrier at a specified temperature.

Unlike the prior art methods of dispersing alumina, which utilize mechanical processes and high shear, the present invention utilizes a functionalized, surface-modified alumina to achieve a homogeneous dispersion of alumina crystallites in an organic polymer.

The elements of the invention will be described in detail hereunder:

Alumina Composition

The alumina composition comprises aluminum oxyhydroxide, aluminum oxide, aluminum hydroxide, or mixtures thereof. The alumina composition is preferably an aluminum oxyhydroxide including boehmite or a pseudoboehmite, most preferably a boehmite alumina.

The alumina composition may be in the form of dry particles, an aqueous slurry, an acidized alumina composition, or mixtures thereof. In a preferred embodiment of the invention, the alumina composition is in the form of an aqueous slurry.

The alumina composition to be utilized by the present method is to be produced in high purity form with a controlled crystallite size. In this regard the alumina composition of the invention may include particles having an average crystallite size of from 3 nm to 60 nm, more preferably of from 4 nm to 45 nm, and most preferably 4 nm to 40 nm as measured by X-ray diffraction on a 120 plane. Further, the alumina composition may include a BET surface area of from 30 to 350 $m^2/g$, preferably a BET surface area of from 50 to 350 $m^2/g$. These measurements were taken after calcination at 550° C. for 3 hours.

In an embodiment of the invention, the starting boehmite alumina composition has a BET surface area (without calcination) of from 50 to about 350 m/g and an average crystallite size of from about 4 nm to about 40 nm as measured by X-ray diffraction on the 120 plane. After 3 hours of calcination at 550 PC, the surface area ranges from about 80 $m^2/g$ to about 300 $m^2/g$.

Organic Modifier

As will be discussed in more detail hereafter, the organic modifier of the present invention bonds with the surface of the alumina and facilitates the exfoliation, or wetting, of the alumina to the nano-scale by various materials.

The preferred organic modifier of the present invention is an acrylic acid composition comprising a monomeric and oligomeric form of acrylic acid. The acrylic acid composition includes target molecules including monomers, dimers, trimers, and oligomers of various molecular weights or repeating monomer units. The acrylic acid composition preferably contains from about 30 to about 59.9% by weight of trimers and larger oligomers.

The organic modifier is mixed in with the alumina so as to distribute it on a crystallite surface of the alumina. The organic modifier agent may be added during the production of the alumina composition or to an alumina slurry as set forth in the method of the invention.

The organic modifier is added in amounts of from 1 to 25 wt % based on the alumina composition, preferably 3 to 7 wt % based on the alumina composition. The percentages are based on preferred alumina compositions of a hydrated powder form.

pH Change

In an optional embodiment of the invention, the alumina composition is in aqueous slurry form. The alumina slurry will typically have a pH of between 8 and 10, preferably 9. The organic modifier including the acrylic acid composition is mixed in with the alumina slurry to form an acidic slurry having a pH of from 2.5 to 4.0, preferably from 2.9 to 3.5.

A base additive is added to modify the pH of this acidic slurry to a slightly less acidic slurry, having a pH of from 4.2 to 5.0, and to attract the organic modifier molecules to the surface of the alumina composition.

Those of ordinary skill in the art of the invention are able to identify bases to use for the process of the invention. However, for clarity, the base additive may be selected from a group comprising potassium hydroxide, sodium hydroxide, calcium hydroxide, ammonium hydroxide, and an amine. The preferred base additive is sodium hydroxide or potassium hydroxide. The addition of the organic modifier together with this pH modification step forms a surface-modified alumina composition.

Drying Step

As is well known by those of skill in the art, typical processes of producing alumina involve a drying step. The drying step is critical to the method of the invention as it is through the elimination of the water that the organic modifier is covalently bonded to the surface-modified alumina composition to form a functionalized, surface-modified alumina composition.

The drying can be by means of direct or indirect heating methods. These methods may include spray dryer, contact dryer, or pan dryer. In a preferred method the reaction takes place in a spray dryer.

The drying process may take place in an inert atmosphere e.g., nitrogen, or in air and depending on what method of drying is selected the drying can take place at temperatures between 85° C. to 250° C., preferably between 100° C. to about 250 PC, most preferably between 105° C. to 120° C. Furthermore, depending of the drying technique selected, a person skilled in the art of the invention will know how long the drying should take and the timing will therefore vary between a few seconds to between 2 and 6 hours.

For example, if the drying is carried out using a spray dryer the drying step is carried out with outlet temperature preferably from about 105° C. to about 120° C. and from a few seconds up to a few minutes. If a contact dryer is used, the equipment can be externally heated with oil that circulates inside an external jacket to the target temperature preferably in the range of 200° C. to 250° C. for only a few minutes. A pan dryer can be used at temperatures of around 100-140° C., preferably 120 to about 140° C. for about 1-2 hours.

Illustrative Embodiments of Methods of the Invention

In a first embodiment of the present invention, the organic modifier of the present invention is mixed under moderate temperature and pressure conditions, with a boehmite aqueous slurry. The slurry and organic modifier are, for example, heated to 105° C. in a closed reactor vessel operated under autogenic pressure for sufficient time, preferably 0.5 to 2 hours. The slurry is then dried in a spray dryer, without any intermediate filtration or washing, to covalently bond the organic modifier to the surface-modified boehmite. The drying is required to remove water from the process as well as to drive the reaction between the organic modifier and the surface-modified boehmite. During the drying process, a small fraction of organic modifier, not bonded to the surface of the alumina, may evaporate. However as only a small amount of organic modifier is present, the drying step produces only a very small amount of evaporated organic modifier.

The result is an alumina powder that contains the bonded organic modifier. The strength of this interaction is such that a minimal amount of organic modifier is sufficient to provide surface modification of the alumina for the preparation of highly concentrated nano-boehmite single particle crystallite dispersible in polymers.

In a second embodiment, the starting alumina is a powder that contains less than 1 wt % formic acid or other short carbon chain monocarboxylic acids. This acidized alumina powder is mixed with deionized water before being combined with the organic modifier, generally at scientific room temperature. The resulting slurry is then dried, without any intermediate filtration or washing, in a contact dryer that is externally heated with circulating oil at about 220° C. and operates under nitrogen gas flow for about 10 minutes to covalently bond the organic modifier to the surface-modified boehmite. All the organic modifier is fully reacted to produce a powder form characterized by organic modifier species anchored to the surface of the boehmite leaving behind no non-bonded acrylic acid.

In a third embodiment, the organic modifier is added to a boehmite aqueous slurry having a pH of 9 until a pH of 2.5 to 4.0 is reached. A base additive is then added to the slurry until a pH of 4.2 to 5.0 is reached. In the presence of the base, the organic modifier reacts readily to provide higher covalent linkage to the alumina as revealed by FTIR spectroscopy, and as will be further illustrated in the Example section below.

All of the methods described herein provide for covalent bonding of the organic modifier to the surface-modified alumina composition to form a functionalized, surface-modified alumina composition. The first embodiment is preferred as it allows for the incorporation of low levels of organic modifier with covalent bonding between the organic modifier and the alumina composition without the addition of extra additives. The first embodiment provides for wet crystallites suspended in aqueous phase such as those obtained as intermediate streams of boehmite during industrial production.

The third embodiment provides for a pH shift that modifies the group of reacted monomers. This is important as it provides for the ability to control the level of incorporation of the organic modifier on the alumina specifically when desired patterns with higher levels of organic modifier are required for specific applications.

It will be appreciated by those of ordinary skill in the art that a combination of all these embodiments can be used to produce optimal structures.

The reactions in all embodiments cause a permanent change of the surface properties of the alumina, due to the strength of the covalent bond involved.

Dispersion in a Carrier

The functionalized, surface-modified alumina composition of the present invention, i.e., surface-modified alumina covalently bonded to the organic modifier, is able to achieve a homogeneous and substantially single crystallite dispersion in a carrier, preferably a waxy carrier, and most preferably a low molecular weight polymer.

As referred to herein, a low molecular weight polymer comprises a polymer having an average molecular weight of from about 3,000 to about 20,000, and a viscosity of from about 100 to about 1,200 cP when at a temperature of 190° C.

Non-limiting examples of suitable waxy carriers include aliphatic liquids, polyethylene, polyethylene terephthalate, polypropylene, waxes, for example Fischer-Tropsch waxes, and other polyolefins.

The modified alumina of the present invention is added to the carrier at a temperature of from about 80° C. to about 300° C., preferably about 170° C. to about 185° C. The functionalized surface-modified alumina can be added in amounts of from 1 to 50 wt % of the carrier, preferably in amounts of from 25 to about 50 wt % of the carrier, most preferably 40% wt of the carrier. This can be done in a melt mixing process.

It has surprisingly been found that when the functionalized surface-modified alumina of the present invention is mixed with the carrier, e.g., a low molecular weight polymer, the carrier acts as a wetting agent which solubilizes the functionalized surface-modified alumina. The functionalized surface-modified alumina thus readily disperses in the carrier with simple mixing, resulting in a homogeneous dispersion.

The functionalized surface-modified alumina is dispersible down to nano-sized single crystallites in an organic polymer. As will be shown more fully hereinafter, the functionalized surface-modified alumina disperses particularly well in a low molecular weight isotactic polypropylene. It will be appreciated though that the modified alumina can be dispersed in any low molecular weight polymeric material or waxy carrier. The surface tension of a waxy carrier can be used to gauge the dispersibility, or wettability, of the modified alumina by that carrier. The surface tension (or surface free energy) range of the functionalized surface-modified alumina produced from the above process is from about 35 dyne/cm to about 60 dyne/cm. Materials having a surface tension which is within or below this range will wet the alumina.

To assess the wettability of the modified alumina by a waxy carrier, place droplets of the waxy carrier in question onto a sample of compacted functionalized, surface-modified alumina powder. A carrier with a surface tension higher than the range set forth above for functionalized, surface-modified alumina will form a distinct droplet on the alumina. The droplets of a carrier with lower surface tensions will become more spread out on the surface of the compact material. As the droplets spread, the angle formed between the droplet and the surface, i.e., the contact angle, decreases. The behaviour of the droplets, namely, the spreading out of the droplets and the reduction of the contact angles, serves as a predictor of the wettability behaviour of the functionalized surface-modified alumina by the waxy carrier in question.

Non-limiting examples of lower surface energy liquids and polymers suitable as carriers in the present invention are aliphatic liquids, polypropylene (surface energy of 31 dyne/cm) and polyethylene (surface energy 33 dyne/cm). Polyethylene terephthalate (surface energy of 44 dyne/com) is an example of a polymer with surface energy which is higher but still within the surface energy range of functionalized surface-modified alumina, as set forth above.

Analytical Methods:

The inherent properties of the products of the present invention were measured using the following analytical techniques.

The alumina compositions are identified using X-ray analyses. The samples are placed into an X-ray diffraction 2" diameter plastic disc with a 1" diameter opening. X-ray diffraction data is acquired using a Bruker AXS D4-ENDEAVOR. Boehmite and pseudoboehmite, aluminum oxide, aluminum hydroxide, or mixtures are identified by X-ray diffraction as described in the A.S.T.M. X-ray Diffraction Index. The boehmite single particle crystallite sizes are obtained by X-ray diffraction technique using X-ray diffraction peaks and the Debye formula.

Figure 6:
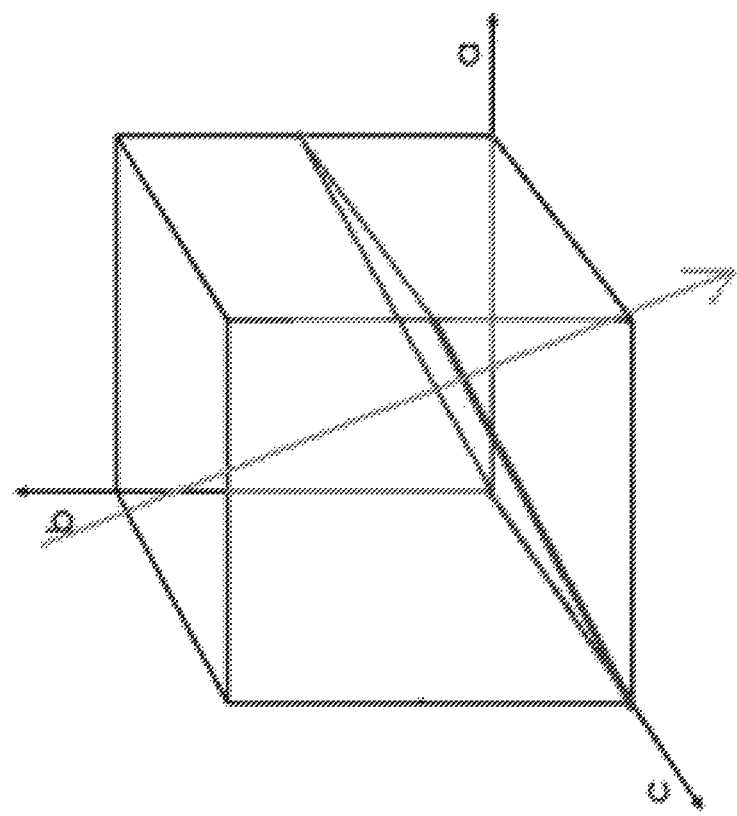
FIG. 6 illustrates the method of measuring the crystallite size in the present invention.

Crystal sizes are expressed by the length obtained for diffraction peak 120. The 120 measurement is the distance along a line perpendicular to the (120) plane, as shown in FIG. 6. Analysis of peak-width on X-ray powder diffraction peaks at 120 gives the values commonly reported for crystallites size.

The measured 120 crystal size is normal (90°) to the 120 plane and is represented by the arrow. This peak (crystal plane) is the most accessible in Boehmite's x-ray diffraction pattern and has been used for the characterization of the alumina composition.

The particle size of the dry powder is determined by light diffraction on a Horiba apparatus. The samples are examined after dispersion in anhydrous iso-propyl alcohol after ultrasonic mixing for a sufficient time to break down the larger agglomerates.

The surface area values are determined by $N_2$ adsorption. Data is collected on heat treated samples at 550° C. for 3 hours. The samples are degassed for 0.5 hours under vacuum at 300° C. Data is collected on a Quantachrome Apparatus. The surface area (m2/g) is evaluated using the B.E.T. equation.

The chemical composition is obtained by means of LECO carbon analyzer. A sample of the powder that contains the organic modifier is weighted in a crucible and placed in a furnace system that operates with pure oxygen. This ensures the complete combustion of all organics in the sample to obtain the carbon content of the sample, as % carbon by weight. Similarly, the organic modifier is analysed and the carbon content of the organic modifier is determined after complete combustion. After the combustion reaction, the amount of organic modifier in the powder, expressed as % carbon by weight, is calculated from the residual total carbon content of the powder by using the following formula:

$$100*Carbon_{powder}/Carbon_{organic\ modifier}$$

where $Carbon_{powder}$ and $Carbon_{organic\ modifier}$ are expressed as % by weight.

The reaction is observed by IR spectroscopy with the appearance of the symmetric stretching band with maximum at about 1580 $cm^{-1}$ and the asymmetric band at about 1460 $cm^{-1}$ which are characteristics of the bridging binding modes of the carboxylate. The frequency shift of the carbonyl group (C=O) from about 1700 $cm^{-1}$ to about 1730 $cm^{-1}$ has been assigned to the perturbation in the vibration mode of the carbonyl group of the acid (C=O) by the interaction with the alumina sites. The surface of the powder is analysed by Diffuse Reflectance Infrared Fourier Transform Spectroscopy.

The characterization of the size of the alumina nano particles in the polymer composition is carried out on films. The film is obtained by weighing 0.05 grams of the polymer composition containing the functionalized surface-modified alumina onto an aluminum plate pre-heated to temperature above the melting point of the composition. The composition is then pressed onto a film using an SEM stub. The film is evaluated on a JEOL 6390LV SEM machine.

To more fully illustrate the present invention, the following non-limiting examples are presented.

Example 1

A boehmite aqueous slurry, 450 lbs at pH of 9, was mixed with an organic modifier formed from a carboxylic acid compound containing acrylic acid oligomers of various acrylic acid molecular weights, The organic modifier had 45% trimer and higher oligomers and a carbon content of 50% by weight. The organic modifier was added in an amount of 3.4% by weight based on the mass of the boehmite and stirred with an impeller at room temperature. The mixture was heated to 105° C. for 2 hours under moderate stirring. The slurry was aged and cooled to room temperature. At this point, the pH of the slurry was 3.1. The slurry was dried using a spray dryer with an inlet temperature of 390° C. and outlet temperature of 110° C. The final powder produced from the spray dryer had a carbon content of 1.2% by weight The amount of organic modifier on the boehmite powder after the process of the invention was 2.4% by weight of the boehmite powder.

The powder consisted of micrometer-scale particles made of agglomerated crystallites of about 40 nm when measured by X-ray diffraction in the 120 plane. The D50 diameter of the particles was approximately 18 microns as measured by light diffraction method. FIG. 1 shows the results of a DRIFT spectra analysis based on aluminum-oxygen-carbon stretching band. The frequency at 1730 $cm^{-1}$ indicates the adsorption of the acid onto the boehmite sites. The peak at 1575 $cm^{-1}$ confirms the covalent bond of the modifier to the surface of the alumina.

Additional trials of Example 1 were run with the outlet temperature of the spray dryer at 105° C. The results were similar, the amount of organic modifier on the boehmite powder ranged from 2.3 wt % to 2.7 wt %.

Example 2

In Example 2, the product obtained according to the procedure of Example 1 was dispersed in crystalline isotactic polypropylene having a softening point of 160° C.

A dual shaft vessel was used for the preparation of the dispersion. The vessel had a capacity of 2 gallons and was provided with two types of agitation systems, an anchor type impeller to homogenize the bulk mass and a Cowles type disperser to disperse the polymer mass wetting the alumina particles. The agitators were operated at sufficient peripheral velocity to homogenize the mass. The mixer was operated at about one half of the maximum allowable RPM range. The vessel was externally heated by circulation of oil into an external jacket. The temperature of the mass was monitored through an internal thermocouple during the whole mixing process. The batch composition included 2.5 Kg of crystalline isotactic polypropylene, and 1.67 Kg of functionalized surface-modified alumina composition produced according to the procedure of the Example 1. The powder content in the resulting polymeric composition was 40% by weight.

First the polymer was melted at temperature of 180° C. Then the functionalized surface-modified alumina powder, 1.67 Kg, was metered in 5 separated steps (334 g at each step), allowing the powder to stir for 30 minutes between each step. This procedure was repeated 4 times. After adding the last of the powder, the system was mixed for 1 hour at 180+/−1° C.

Figure 2:
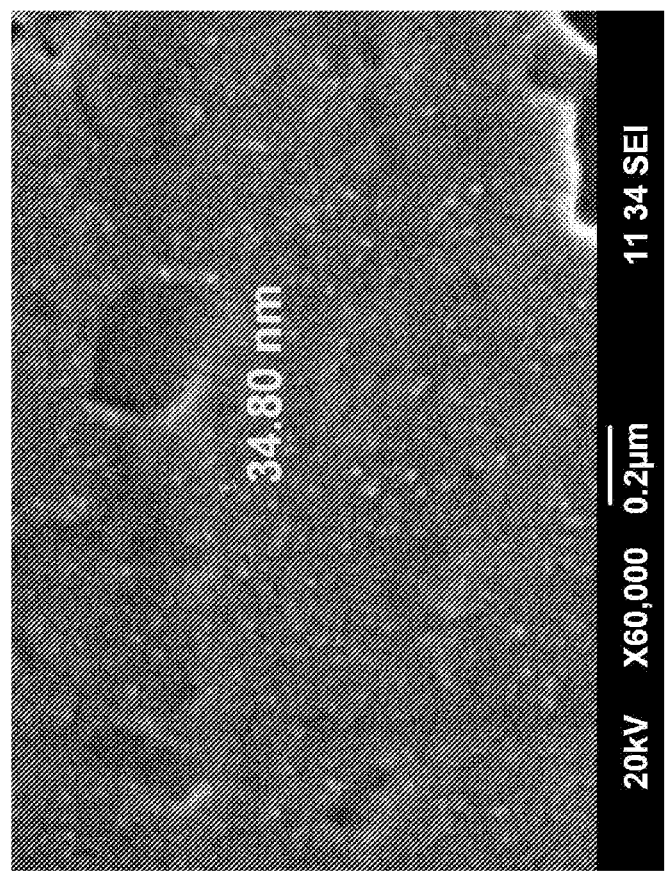
FIG. 2 shows results of scanning electron microscopy (SEM) imaging of a sample of functionalized surface-modified alumina dispersed in polypropylene as per Example 2.

FIG. 2 shows the results of scanning electron microscopy (SEM) imaging of a sample of the functionalized surface-modified alumina dispersed in the polypropylene. The sample was prepared by weighing 0.05 grams of the polypropylene composition containing the functionalized surface-modified alumina onto an aluminum plate pre-heated to about 185° C. The composition was then pressed onto a film using an SEM stub. As shown in FIG. 2, the alumina particles dispersed uniformly in the polypropylene with the size of the alumina particles consistent with the dimension of single particle crystallites of the functionalized surface-modified alumina of Example 1.

Example 3

In Example 3, 50 pounds of boehmite alumina powder containing less than 1 wt % of formic acid was mixed with 438 pounds of deionized water and 1.64 pounds of organic modifier. The concentration of the organic modifier was 3.3% by weight of the boehmite powder added to the reactor. The slurry was stirred at room temperature for 2 hours. A portion of the slurry was dried in a contact dryer operated under a nitrogen gas flow. The final modified alumina powder produced had a content of organic modifier equal to 3.3% by weight of boehmite powder which indicated that all the amount of the organic modifier initially added was retained on surface of the alumina.

Figure 3:
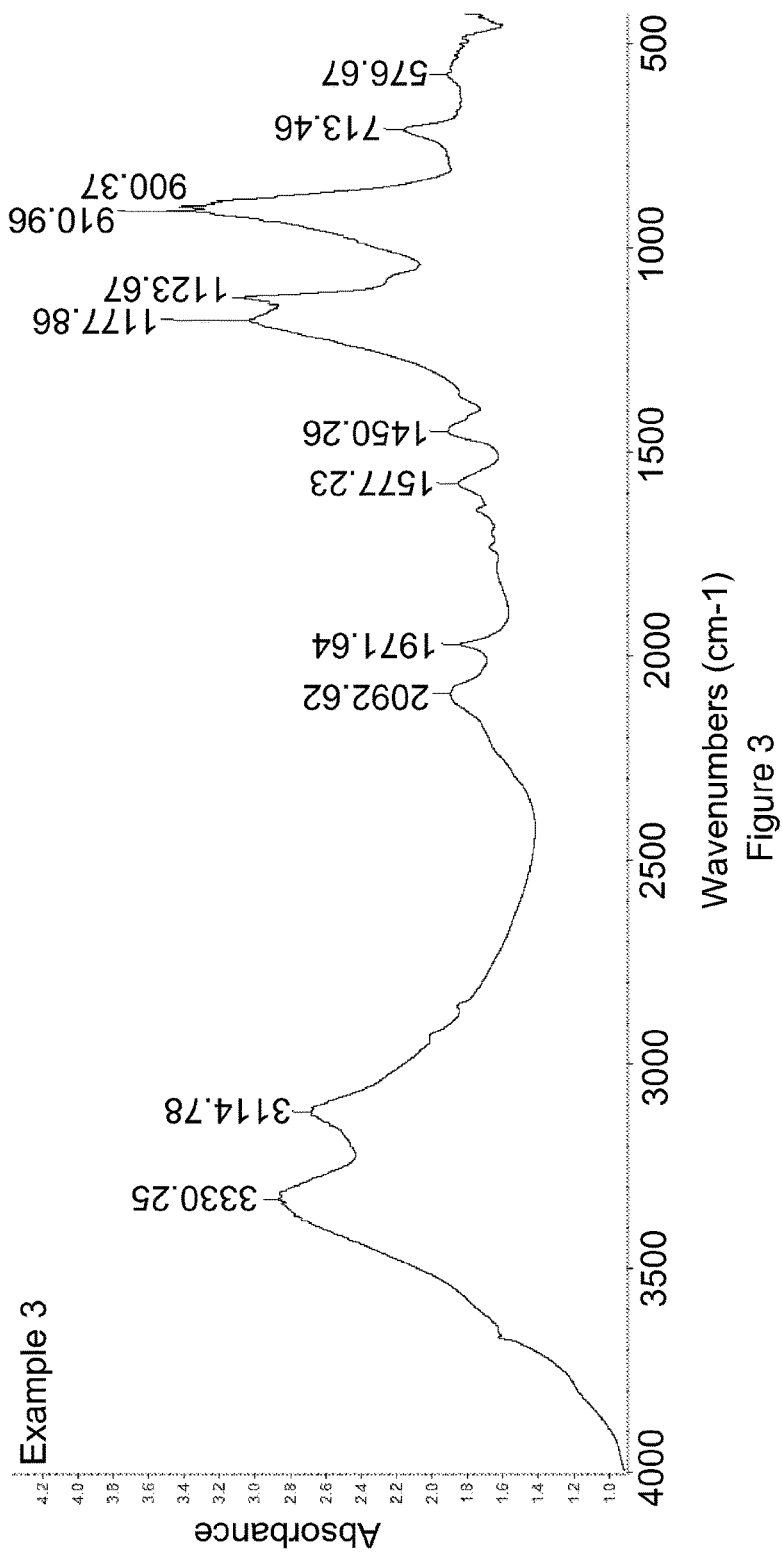
FIG. 3 shows results of a DRIFT spectra analysis based on alumina-oxygen-carbon stretching band as per Example 3.

FIG. 3 shows the results of a DRIFT spectra analysis based on aluminum-oxygen-carbon stretching band at 1577 cm-1.

The examples above show the unexpected result of homogeneous dispersion on the nano-scale of the functionalized surface-modified alumina using a minimal amount of organic modifier. Complete dispersion was achieved using only 3-4 wt % organic modifier. The polymer acted as a solvent, wetting and dissolving the functionalized surface-modified boehmite particles.

Comparative Example 1

Figure 4:
FIG. 4 shows a dispersion sample as per Comparative Example 1 comparing the dispersion of a sample prepared as per the method of Example 2 and a sample prepared using unmodified alumina.

Comparative Example 1 serves as a comparison of the present invention by dispersing boehmite that has not been surface-modified. A sample of dispersion in isotactic polypropylene having a softening point of 160° C. was prepared according to the procedure of Example 3 using unmodified boehmite powder. The powder could not be dispersed. The results are shown in FIG. 4.

Example 4

In a glass reactor with anchor type impeller a boehmite alumina slurry, 2.53 lbs having a pH of 9, was mixed at room temperature with 0.0143 lbs of the organic modifier in an amount of 5.5% by wt based on the mass of the boehmite. At this point the pH of the slurry was 3.5. The pH was adjusted to a value of 4.5 by metering in 0.00447 lbs of 10 M sodium hydroxide solution. The mixture was heated to 105° C. for 2 hours while stirring. The slurry was aged and cooled to room temperature. The slurry was dried using a spray dryer with air inlet temperature of 350° C. and outlet temperature of 110° C. The final powder produced from the spray dryer had a carbon content of 2.5% by wt. based on the amount of $Al_2O_3$. The amount of modifier on the functionalized, surface-modified alumina powder was 4.1% by wt. based on the content of the boehmite powder.

Example 5

A sample was prepared where an organic modifier was mixed with a boehmite aqueous slurry in the same amount of the Example 4 but no base additive was used. The resulting amount of modifier on the functionalized, surface-modified alumina powder was 3.7% by wt based on the content of the powder instead of 4.1% by weight obtained by pH adjustment method.

Figure 5:
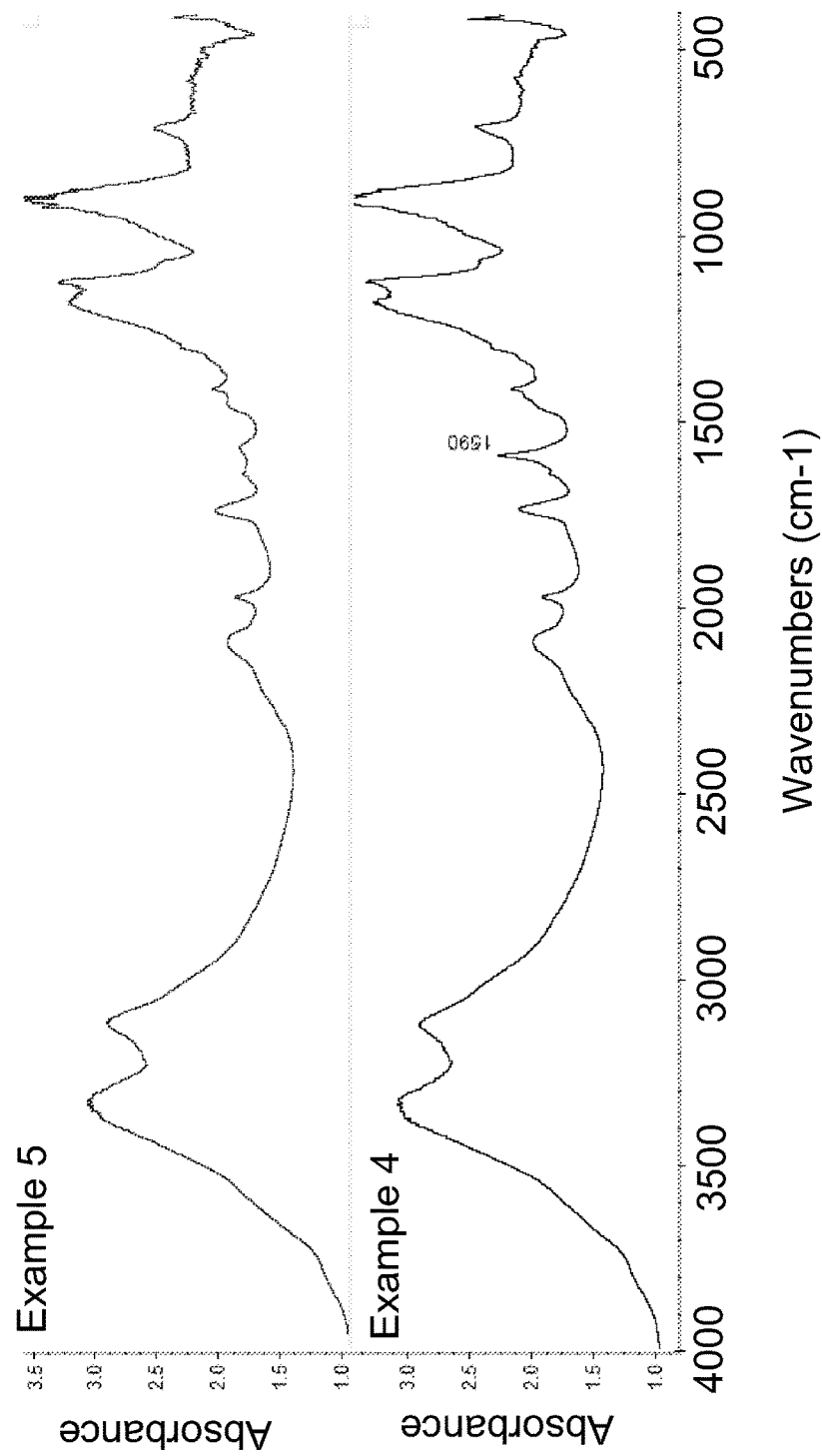
FIG. 5 shows results of a DRIFT spectra analysis based on aluminium-oxygen-carbon stretching band as per Example 4 and Example 5.

FIG. 5 shows the results of a DRIFT spectra analysis of the modified alumina product obtained through the procedure of Example 4 and Example 5. The higher adsorbency in the region of 1590 cm$^{-1}$ of the Example 4 in comparison to Example 5 is due to the groups aluminum-oxygen-carbon stretching vibration modes which are present in higher concentration on the modified surface of boehmite. This shows that there is more of the organic modifier present on the functionalized, surface-modified surface of the boehmite prepared according to the procedure of the Example 4 when compared to Example 5.

Example 6

In another trial, an organic modifier was mixed with a boehmite aqueous slurry in the same amount as Example 4 but, instead of adding a base additive and carrying out the aging step at the temperature condition and time of the Example 4 and drying, the slurry was first heated to 105° C. and aged for 2 hours at pH of 3.5 under moderate stirring, and subsequently the pH was adjusted to 4.5 with the same amount of base additive added in the Example 4. The slurry was dried at the same temperatures of Example 4 with a spray dryer. The amount of modifier on the boehmite powder after drying was 3.5% by wt compared to 4.1% by weight obtained by pH adjustment method of the Example 4. Examples 5 and 6 show that the pH modification must be applied to the alumina composition before an aging step to provide the enhancement of the improved attachment of the organic molecules to the surface of boehmite.

Although specific embodiments of the invention have been described herein in some detail, this has been done solely for the purposes of explaining the various aspects of the invention, and is not intended to limit the scope of the invention as defined in the claims which follow. Those skilled in the art will understand that the embodiment shown and described is exemplary, and various other substitutions, alterations and modifications, including but not limited to those design alternatives specifically discussed herein, may be made in the practice of the invention without departing from its scope.

The invention claimed is:
1. A method for producing a functionalized surface-modified alumina including the steps of:
   a. providing an alumina composition;
   b. adding an organic modifier comprising a monomeric and oligomeric form of acrylic acid composition to the alumina composition to produce a surface-modified alumina composition; and
   c. drying the surface-modified alumina composition to produce a functionalized, surface-modified alumina composition wherein the organic modifier is covalently bonded to the surface-modified alumina composition.
2. The method of claim 1, wherein the alumina composition comprises aluminum oxyhydroxide, aluminum oxide, aluminum hydroxide, or mixtures thereof.
3. The method of claim 2, wherein the aluminum oxyhydroxide is boehmite or pseudo-boehmite.
4. The method of claim 1, wherein the alumina composition comprises a BET surface area of from 30 to 350 m$^2$/g.
5. The method of claim 1, wherein the alumina composition comprises particles having an average crystallite size of from 3 nm to 60 nm as measured by X-ray diffraction on a 120 plane.
6. The method of claim 1, wherein the acrylic acid composition comprises 30 to 59.9% by weight of trimers and higher oligomers.
7. The method of claim 1, wherein the organic modifier is added in amounts of from 1 to 25 wt % based on the alumina composition.
8. A method for producing a functionalized surface-modified alumina including the steps of:
   a. providing an alumina composition in an aqueous slurry form, the slurry having a pH of from 8 to 10;

b. adding an organic modifier comprising an acrylic acid composition to the slurry to form an acidic slurry having a pH of 2.5 to 4.0;

c. adding a base additive to the acidic slurry to increase the pH of the acidic slurry to a pH of 4.2 to 5.0 to form a surface-modified alumina composition; and d. drying the surface-modified alumina composition to produce a functionalized, surface-modified alumina composition wherein the organic modifier is covalently bonded to the surface-modified alumina composition.

9. The method of claim 8 wherein the pH of the alumina composition in the aqueous slurry is 9.

10. The method of claim 8, wherein the base additive added to the acidic slurry comprises sodium hydroxide or potassium hydroxide.

11. A method of producing alumina which is dispersible into nano-sized single particle crystallites in an organic polymer including the steps of:

a. providing the functionalized, surface-modified alumina as prepared according to the method of claim 1; and b. adding the functionalized, surface-modified alumina to a carrier at a temperature of from scientific room temperature to 300° C.

12. The method of claim 11, wherein the carrier comprises a waxy carrier.

13. The method of claim 11, wherein the carrier comprises a low molecular weight polymer.

14. The method of claim 11, wherein the functionalized, surface-modified alumina is added in amounts of from 1 to 50 wt % of the carrier.

15. The method of claim 11 wherein the functionalized, surface-modified alumina is dispersible down to nano-sized, single crystallites in an organic polymer.

16. The method of claim 11 wherein the functionalized, surface-modified alumina which is dispersible into nano-sized, single crystallites in an organic polymer, has a surface tension of from 35 dyne/cm to about 60 dyne/cm.

* * * * *